US012788491B2

(12) United States Patent
Isola et al.

(10) Patent No.: US 12,788,491 B2
(45) Date of Patent: Nov. 10, 2026

(54) PLANNING DEVICE FOR POSITIONING TREATMENT APPLICATORS

(71) Applicant: KONINKLIJKE PHILIPS N.V., Eindhoven (NL)

(72) Inventors: Alfonso Agatino Isola, Eindhoven (NL); Guillaume Leopold Theodorus Frederik Hautvast, Veldhoven (NL); Martina Ciancarella, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 220 days.

(21) Appl. No.: 18/712,864

(22) PCT Filed: Nov. 23, 2022

(86) PCT No.: PCT/EP2022/082920

§ 371 (c)(1), (2) Date: May 23, 2024

(87) PCT Pub. No.: WO2023/099299

PCT Pub. Date: Jun. 8, 2023

(65) Prior Publication Data

US 2025/0017658 A1 Jan. 16, 2025

(30) Foreign Application Priority Data

Dec. 3, 2021 (EP) .................................... 21212152

(51) Int. Cl.
*A61B 34/10* (2016.01)
*A61B 18/00* (2006.01)

(52) U.S. Cl.
CPC .... *A61B 34/10* (2016.02); *A61B 2018/00547* (2013.01); *A61B 2018/00577* (2013.01); *A61B 2034/107* (2016.02)

(58) Field of Classification Search
CPC .............. A61B 2017/3411; A61B 2018/00577
See application file for complete search history.

(56) References Cited

U.S. PATENT DOCUMENTS

| | | | |
|---|---|---|---|
| 11,291,863 | B2 | 4/2022 | Isola |
| 2012/0197058 | A1 | 8/2012 | Shukla |

(Continued)

FOREIGN PATENT DOCUMENTS

| | | | | |
|---|---|---|---|---|
| EP | 3777748 A1 | 2/2021 | | |
| WO | WO9948558 | 9/1999 | | |
| WO | WO-2017028934 A1 * | 2/2017 | ............. | G06T 11/10 |

OTHER PUBLICATIONS

PCT International Search Report, International application No. PCT/EP2022/082920, Mar. 7, 2023.

*Primary Examiner* — Colin T. Sakamoto

(57) ABSTRACT

The invention relates to a planning device (2) for positioning treatment applicators (8). The device (2) comprises a providing unit (4) configured for providing a distance r to be considered between applicator entry points (10) and a processor (6). It has been found that when utilizing treatment applicators, in particular ablation treatment applicators, placing two or more applicators closely together increases the risk of ablating and damaging more tissue than required for the therapy success. By configuring the processor (6) to inactivating all entry points within a distance r from a currently selected entry point such that these entry points are unavailable to further optimization iterations, and then conducting a further optimization iteration, an optimal applicator configuration can be provided that is effective with regard to the therapy success while the risk of ablating more tissue than required is reduced.

17 Claims, 7 Drawing Sheets

(56) References Cited

U.S. PATENT DOCUMENTS

| | | | | |
|---|---|---|---|---|
| 2019/0008591 | A1* | 1/2019 | Desai | G06T 7/0012 |
| 2019/0209245 | A1* | 7/2019 | Sparks | G06T 19/003 |
| 2020/0001118 | A1 | 1/2020 | Snider, III | |
| 2022/0039831 | A1* | 2/2022 | Gowda | A61B 17/3403 |
| 2022/0265359 | A1 | 8/2022 | Isola | |

* cited by examiner

PLANNING DEVICE FOR POSITIONING TREATMENT APPLICATORS

FIELD OF THE INVENTION

The invention relates to a planning device and system for positioning treatment applicators, as well as to a planning method and computer program for positioning treatment applicators.

BACKGROUND OF THE INVENTION

The use of treatment applicators utilizing thermal ablation or forms of radiation therapy is getting increasingly popular for cancer treatments due to their applicability to non-resectable tumors and the rapid recovery of the patient.

For such treatments, an optimal placement of the applicators is crucial, which is often determined based on the tumor position and size, the device manufacturers' specifications, and the physician's experience. While it is common to utilize a manual placement of ablation devices, also image-guided systems are known, for example from US 2019/0008591 A1 and EP 3 777 748 A1.

It has been found, however, that during such treatment efforts physical interference between applicators may occur that damage more tissue than necessary for the therapy success.

SUMMARY OF THE INVENTION

It is an object of the present invention to provide a planning device and system for positioning treatment applicators, as well as a planning method and computer program for positioning treatment applicators like ablation treatment applicators to improve applicator positioning.

In a first aspect, a planning device for positioning treatment applicators is presented. The device comprises a providing unit configured to provide a distance to be considered between applicator entry points, and a processor configured to conduct an optimization iteration step which determines an optimal applicator configuration comprising a first applicator entry point, inactivate all entry points within the distance from the first applicator entry point such that these entry points are unavailable to further optimization iteration steps, conduct a further optimization iteration step which determines an optimal applicator configuration comprising a further applicator entry point.

This approach has the advantage of reducing the freedom of the device to select entry points only progressively along the iterations. At the very beginning, all entry points will be active and selectable by the algorithm that will be described in more detail subsequently. However the more entry points are selected during iterations, the more constrained the search and solution space will become, since more and more entry points will become inactive. The solution produced by such a technique will ensure that a distance defined by the user is complied with.

It has been found that by utilizing said device, treatments like thermal ablation or brachytherapy can be improved. In particular, a reduced physical interference between used applicators is achieved. This leads to reduced overlap among delivered ablation zones and thus lowers the risk to ablate the same tissue multiple times. Moreover, a reduced number of ablation or brachytherapy applicators needs to be placed compared to known treatment procedures.

In one embodiment the device provides positioning support for ablation treatment applicators, wherein the processor is further configured to receive a three-dimensional medical image data descriptive of a subject and receive a desired ablation volume, wherein the desired ablation volume is registered to the three-dimensional medical image data. The term desired ablation volume is a label for a particular ablation volume. The desired ablation volume is registered to the three-dimensional medical image data. That is to say the desired ablation volume marks a region or identifies a region of the three-dimensional medical image data.

The processor is further configured to receive one or more protected volumes, wherein the one or more protected volumes are registered to the three-dimensional medical image data. The one or more protected volumes may for example be volumes which could injure the subject if they are sonicated or ablated too much. For example, the one or more protected volumes may be used to protect organs or critical anatomical structures.

The processor is further configured to generate a discrete set of ablation applicator positions registered to the three-dimensional medical image data. In this case the locations around the desired ablation volume may be used to generate a pattern or set of discrete ablation applicator positions. These for example could be generated using a predetermined pattern or algorithm for generating the discrete set.

The processor is further configured to receive a discrete set of ablation patterns. The discrete set of ablation patterns comprises multiple ablation patterns. The discrete set of ablation patterns could be ablation patterns for a single applicator, for example oriented in different directions and/or with different amounts of power supply. In other examples the discrete set of ablation patterns may be from multiple applicators.

The processor is further configured to initialize a composite ablation binary mask registered to the three-dimensional medical image data. For example, the step of initializing the composite ablation binary mask may be to create a blank or unused composite ablation binary mask. The term composite ablation binary mask is used to identify a particular binary mask. The composite ablation binary mask in this case is an ablation binary mask that stores the composite or intersection of all the ablation patterns that are used.

The processor is further configured to determine an unablated volume by comparing the composite ablation binary mask to the desired ablation volume, wherein the unablated volume is registered to the three-dimensional medical image data. The composite ablation binary mask may be used to identify regions that have already been ablated or are intended to be ablated using the configurations on the sequential ablation applicator configuration list. A comparison between the desired ablation volume and the composite ablation binary mask can be used to find a region which still needs to be ablated or additional applicators added so that ablation occurs.

The processor is further configured to determine an applicator configuration comprising at least one applicator entry point using a chosen objective function dependent upon the one or more protected volumes, the unablated volume, the discrete set of ablation patterns, the discrete set of ablation applicator positions, and inactivated applicator entry points.

The chosen applicator configuration specifies one of the discrete set of applicator entry points and one of the discrete set of ablation patterns. In this step, a chosen objective function can be used to evaluate the various combinations of the discrete set of ablation patterns in each of the discrete set of applicator entry points.

The chosen objective function is used to choose the best choice. The chosen objective function may be used to objectively measure such things as coverage of the unablated volume as well as avoiding the one or more protected volumes.

The processor is further configured to update the composite ablation binary mask by calculating a union between the composite ablation binary mask and the one of the discrete set of ablation patterns located at the one of the discrete set of ablation applicator positions.

After the applicator entry point configuration is done, this choice is then used to update the composite ablation binary mask. The above embodiment applies to both multiple applicators being inserted into a subject at the same time and also to applicators which are inserted sequentially.

The chosen objective function may comprise a quadratic ablation coverage-based objective function, a minimum/maximum ablation coverage function, and a uniform quadratic coverage function. A use of any of these functions may be beneficial because they are effective at both choosing regions to ablate as well as protecting critical regions which are specified in the one or more protected volumes.

In a preferred embodiment, the entry points are at least one of the following: grid holes of a grid template, skin entry points. The grid template can be one of the following: rigid grid template, flexible grid template, in particular transperineal grid template, breast template, flexible lead template, grid attached to gynecological (GYN) applicator. Said templates may be used to segment regions of interests, such as target lesions and risk organs.

In one embodiment, no template is used. In this embodiment, the entry points are skin entry points.

In one embodiment, the distance can be at least one of the following: minimum distance in a template or skin surface plane, in particular a minimum Euclidean distance, maximum distance in a template or skin surface plane, in particular a maximum Euclidean distance. The distance can further be a minimum and/or maximum distance between applicator trajectories. Generally, the inactivation of all entry points is based on the first applicator entry point and the distance from the first application entry point.

According to one embodiment, further optimization iterations are conducted until no further optimal applicator configuration is determinable considering the inactivated grid holes or entry points.

In a preferred embodiment, the processor is further configured to conduct a refinement iteration step at which an applicator configuration is removed from the solution and replaced by another applicator configuration, and a further optimization iteration step is conducted to determine an optimal applicator configuration.

With the help of this, the greediness of the iterative optimization is reduced. When an applicator configuration is removed, all the nearby entry points or grid holes that were previously inactivated will be made active and made available for solver selection again.

In one embodiment, in each refinement iteration step the applicator configuration to be removed is selected orderly, i.e. one-by-one, from the optimal applicator configurations. For example, the applicator configuration to be removed can be selected based on a list of all applicators, wherein the applicator configurations to be removed can be automatically selected subsequently, i.e. one after the other, from the list, for instance, until all applicator configurations of the applicator list have been removed at least once or any other abortion criterion is met.

In another embodiment, the refinement iterations are stopped when every applicator configuration was removed once during the iterations or when the removed applicator configuration is determined again as the result of the iteration step.

In an embodiment, in each refinement iteration step the applicator configuration to be removed is selected by means of coverage-based functional values or derivatives to select a least optimal applicator configuration. Coverage-based functional values are values quantifying a coverage that a set of applicator configurations provides to a region of interest, for example, a tumor. Thus, an applicator configuration can be removed from the solution and a coverage-based functional value can be determined for the remaining applicator configuration. This can be repeated and a remaining applicator configuration can be determined for which the coverage-based functional value and thus the coverage of the region of interest is changed least with respect to the full set of applicator configurations. The removed applicator configuration is then the least optimal applicator configuration and can be selected. Accordingly the least optimal applicator configuration refers to the applicator configuration that changes the coverage-based functional value the least with respect to the coverage-based functional value of the full set of applicator configurations.

The providing unit can comprise at least one of the following: graphical user interface, configuration file, database. Generally the providing unit is configured to provide the distance to be considered between applicator entry points to the processor. Moreover, the providing unit can also be a receiving unit for receiving the distance, for instance, from a storage or a user input, and providing the same to the processor for further processing.

The device can further comprise a graphical user interface configured to visualize at least one of the following: optimal set of applicator positioning configurations, inactivated entry points, distance to be considered between entry points.

The graphical user interface of the providing unit and the graphical user interface of the device may be the same graphical user interface or differ from each other.

The graphical user interface may comprise at least one of the following: Text field, continuous slider, discrete slider, radio button or pull-down menu, scroll-wheel interaction while visualizing radius on top of grid/patient anatomy.

The device may be configured for being updated, in particular on demand after changing setting as implemented and/or in real-time upon changing settings.

In another aspect of the present invention, an ablation system is presented. The system comprises an ablation treatment applicator and a planning device as defined in any of claims 1-12.

The ablation treatment applicator my utilize at least one of the following ablation principles: Focused Ultrasound (FU), Microwave (MW), Radiofrequency (RF), Focal Laser Ablation (FLA), Cryo-ablation, Irreversible Electroporation (IRE), or Brachytherapy.

Applicable treatment organs can be prostate, breast, kidney, liver, cervix.

Applicable treatment workflows can be focal, quadrant, hemi-gland prostate, whole-gland prostate, partial breast treatment. Said classifications depend upon the goal of the ablation procedure. A focal treatment may affect only a small area within the prostate, a quadrant treatment a quadrant portion of the prostate gland, a hemi-gland treatment typically affects half of the gland, wherein a whole-gland treatment affects the complete gland. A partial breast treatment is directed towards ablating the breast partially.

In a further aspect of the present invention, a planning method for positioning treatment applicators is presented, the method comprises providing a distance to be considered between entry points and geometric information of a target to be treated, conducting an optimization iteration step which determines an optimal applicator configuration comprising a first applicator entry point based on the geometric information of the target to be treated, inactivating all applicator entry points within the distance from the first applicator entry point such that these entry points are unavailable to further optimization iteration steps, conducting a further optimization iteration step which determines a further optimal applicator configuration comprising a further applicator entry point based on the geometric information of the target to be treated.

It has been found that by utilizing said method, treatments like thermal ablation or brachytherapy can be improved. In particular, a reduced physical interference between used applicators is achieved. This leads to reduced overlap among delivered ablation zones and thus lowers the risk to ablate the same tissue multiple time. Moreover, a reduced number of ablation or brachytherapy applicators needs to be placed compared to known treatment procedures.

In one embodiment, the entry points are at least one of the following: grid holes of a grid template, skin entry points.

In yet another aspect, a planning computer program for positioning treatment applicators is presented, the computer program comprising program code means for causing a computer to carry out the steps of the method as defined in claim 14.

It shall be understood that the device for providing positioning support for treatment applicators of claim 1, the ablation system of claim 13, the method for providing positioning support for treatment applicators of claim 14, and the computer program of claim 15, have similar and/or identical preferred embodiments, in particular, as defined in the dependent claims.

It shall be understood that a preferred embodiment of the present invention can also be any combination of the dependent claims or above embodiments with the respective independent claim. These and other aspects of the invention will be apparent from and elucidated with reference to the embodiments described hereinafter.

DETAILED DESCRIPTION OF EMBODIMENTS

Figure 1:
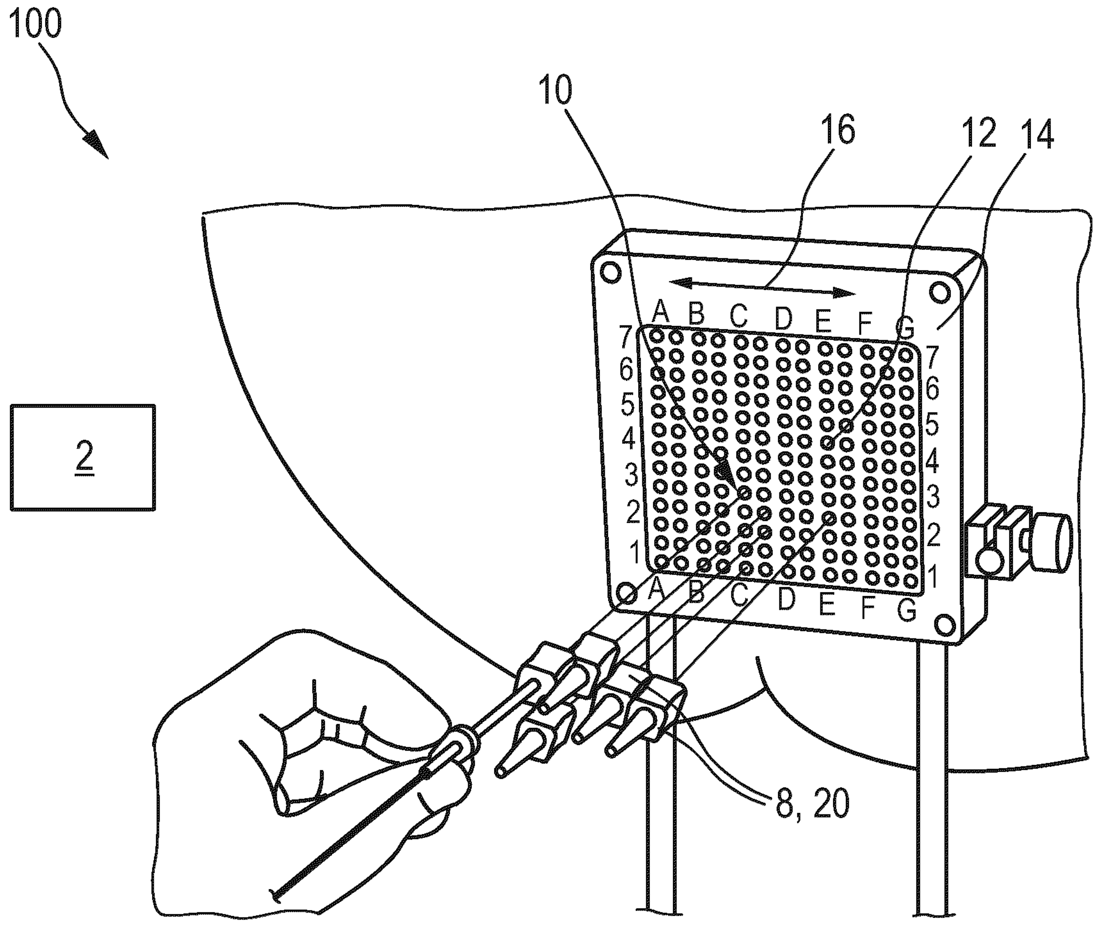
FIG. 1 shows schematically and exemplarily an embodiment of an ablation systems comprising an ablation treatment applicator and a positioning support device.

FIG. 1 shows an ablation system 100. The ablation system 100 comprises treatment applicators 8 that are configured as ablation treatment applicators 20 for percutaneous cancer treatments. The ablation treatment applicators 20 may utilize for example Focused Ultrasound (FU), Microwave (MW), Radiofrequency (RF), Focal Laser Ablation (FLA), Cryoablation, Irreversible Electroporation (IRE) or Brachytherapy. All these therapy modalities require the insertion of applicators 8 into the tumor or affected organ. In order to facilitate positioning the applicators 8, a grid template 14 comprising grid holes 12 is utilized. The applicators 8 are inserted into the grid holes 12 of the grid template 14. The grid holes 12 are an example of entry points 10. Depending on a therapy plan, applicators 8 are inserted into certain grid holes 12 to treat the affected organ or tumor.

Figure 2:
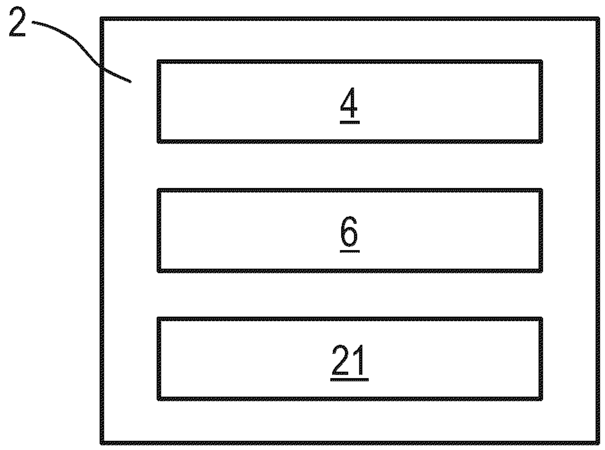
FIG. 2 shows schematically and exemplarily an embodiment of the positioning support device.

In order to support the user in positioning the applicators 8, the ablation system 100 comprises a device 2 for providing position support for the treatment applicators 8. The device 2 comprises a providing unit 4 as shown in FIG. 2. The providing unit 4 is configured for providing a distance r to be considered between applicator entry points 10. These applicator entry points 10 may be grid holes 12 of the grid template 14, as shown in FIG. 1, or arbitrary skin entry points, also called free hand entry points. The providing unit may comprise a graphical user interface, a configuration file or a database. The device 2 furthermore comprises a graphical user interface 21 configured to visualize a set of applicator positioning configurations to finally assist the user in inserting the applicators 8 into the grid holes 12 of the grid template 14 or arbitrary skin entry points.

Figure 3:
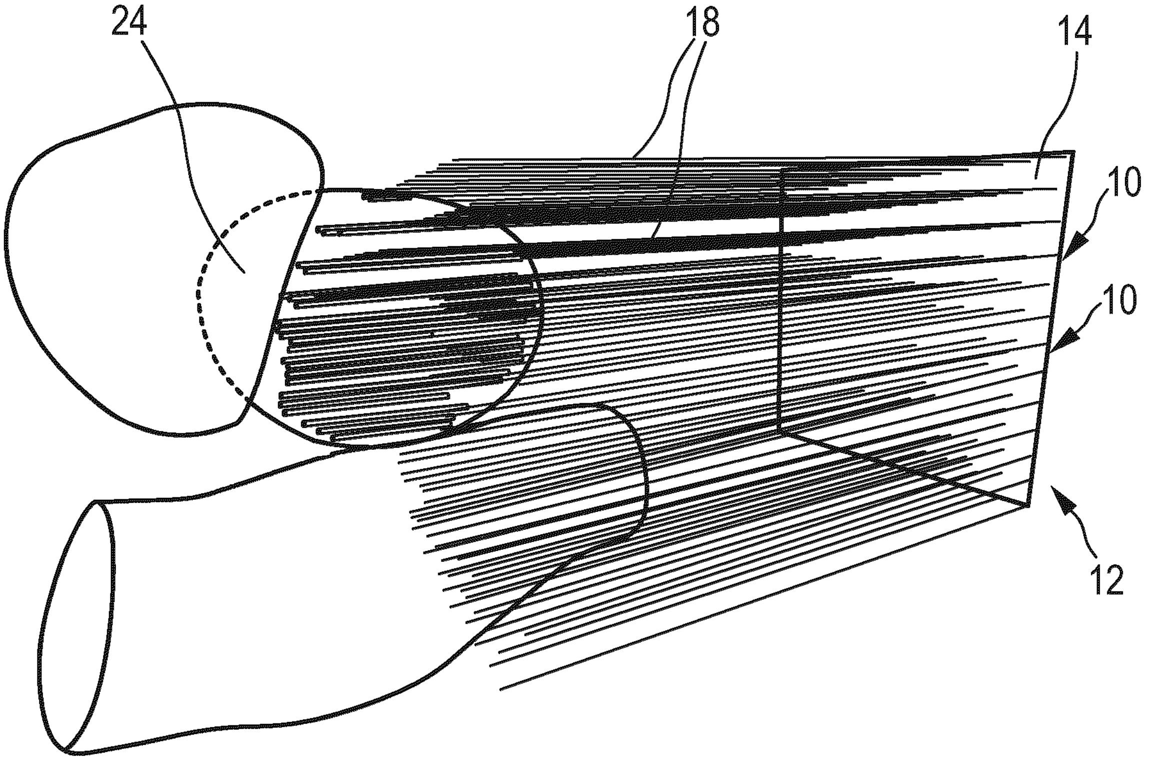
FIG. 3 illustrates the use of a grid template to provide positioning support for treating an organ.

The distance r which is to be considered between applicator entry points 10 is a distance in a surface plane 16 of the grid template 14, as shown in FIG. 1. FIG. 3 shows an example of different applicator trajectories 18 leading towards an organ 24 to be treated.

Referring to FIG. 2 again, the device 2 furthermore comprises a processor 6. The processor 6 of the device 2 is configured to conduct an optimization iteration step which determines an optimal applicator configuration comprising a first applicator entry point 10 and inactivating all entry points 22 within the distance r from the currently selected entry point 10 such that these entry points 22 are unavailable to further optimization iterations. The processor 6 is further configured to conduct a further optimization iteration step which determines a further optimal applicator configuration comprising a further applicator entry point 10.

Subsequently, an example of optimization iteration steps which determine an optimal applicator configuration is described. This known approach is extended herein by considering and inactivating all entry points 22 within the distance r from the currently selected entry point 10 such that these entry points 22 are unavailable to further optimization iterations. Examples may provide for a discrete inverse planning optimization or a mixed discrete-continuous inverse planning optimization approach. Hereto, the clinical expert is only asked to provide following inputs: a set of segmented regions of interest, such as three dimensional medical image data and the one or more protected volumes, a set of clinical goals to achieve, such as a desired ablation volume, and ablation specifications, such as a discrete set of ablation patterns for the applicators to be used. Then, a set covering iterative greedy algorithm is used to find the optimal minimum number of ablation device configurations that can satisfy as well as possible the provided clinical protocol goals. A greedy algorithm searches for a local minimum.

Application of the example may comprise one or more of the following steps. In step 0, the planner takes care to provide a set of segmented regions of interest. This process may be done automatically or based on user input. The segmentation into cancerous, risk, and healthy tissue is of interest. The planner will also take care to translate a prescribed clinical protocol (i.e., a list of prescribed clinical goals/constraints) to corresponding ablation-based mathematical objective functions (e.g., convex quadratic functions) which will be optimized during the subsequent optimization steps. Given the ablation device supplier data, corresponding ablation binary masks are generated for all power-time settings provided in the device datasheet. A 3D grid of potential applicator tip positions and applicator orientations are sampled. Finally, a discrete set of ablation device configurations is generated by combining the set of sampled 3D applicator tip positions/directions with all supplier data-based ablation binary masks related to all possible power-time settings.

According to step 1, the current best applicator configuration that minimizes the ablation-based objective function value is selected from the discrete set generated at step 0. In step 2, given a new set of selected applicator configurations at step 1, the corresponding applicators positions are locally refined along with the corresponding ablation binary masks. As previously done at step 1, here an ablation-based objective function is used to guide the optimizer towards the optimal set of applicators tip positions, orientations and delivered ablation binary masks. According to step 3, steps 1 and 2 are executed repeatedly until a solution satisfying all clinical constraints is reached, and/or the user-defined maximum number of applicators was selected.

Another aspect to examples is the optimization problem definition is described in the steps below. Initially, an optimization problem is defined. The tissue volume under consideration is segmented into structures and binary masks $S_k$ are provided for each k-th structure of interest (i.e. tumor, organs at risk, normal tissue, etc.).

The physician prescribes a clinical protocol with a list of all ablation coverage-based goals that need to be satisfied. A typical goal in thermal ablation therapy is the delivery of conformed ablation over locally cancer cells while sparing as much as possible all nearby healthy tissues. This goal is challenging because ablation of large target volumes conflicts with normal tissue ablation-induced damage tolerance.

Before introducing a set of ablation coverage-based objective functions, a mathematical representation is needed for the delivered ablation zone of a single applicator configuration, and for the composite ablation produced by the delivery of multiple applicator configurations.

Thereafter, the initial discrete set of ablation applicator configurations is generated. Given a supplier device datasheet, the expected ablation zone for each j-th combination of ablation power and delivery time values is converted to a corresponding 3D ablation binary mask:

$$A_j(x) = \begin{cases} 1 & \text{if the position } x \text{ is inside the expected ablated zone} \\ 0 & \text{otherwise} \end{cases} \quad \text{(E1)}$$

A discrete set C of $N_c$ applicator configurations is built. Here, each applicator configuration consists of a combination of discretized applicator paths (i.e. skin insertion point, direction and final applicator tip position), and the expected binary mask $A_c$ produced by a power-delivery time setting. In order to keep a moderately low cardinality $N_c$ for the set C, only applicator configurations with binary masks at least partly overlapping the tumor region will be considered. Moreover, thanks to a subsequent local refinement of the discrete positions and directions of the best selected applicators, a moderate sampling factor and a coarse spatial discretization of the applicator positions and directions can be used to populate the set C.

Finally, when multiple ablation device configurations are delivered, the composite ablation binary mask A is defined as the union of all related ablation binary masks $A_s$:

$$A = \bigcup_s A_s \quad \text{(E2)}$$

A notion of ablated fractional volume is used in the following for quantifying the amount the volume of a structure that is affected by ablation. Given a k-th segmented structure, its currently ablated fractional structure volume $v_k$ produced by a composite ablation binary mask A is given by:

$$v_k(A, S_k) = 100 \cdot \frac{|A \cap S_k|}{|S_k|} \quad \text{(E3)}$$

Here $S_k$ indicates the binary mask of the k-th segmented region of interest, $|\cdot|$ is the cardinality (i.e. the size) operator, and $|A \cap S_k|$ indicates the cardinality of the intersection between the cumulative ablated volume and the structure (i.e. the portion of segmented structure which is currently ablated).

Generally, clinical goals for all regions of interest are translated into corresponding two- or one-sided closed proper ablation coverage-based functions of class $C^2$ $f_1(A), \ldots, f_m(A)$: $\Omega \rightarrow \mathbb{R}$.

In order to achieve a required ablation coverage of the tumor while sparing as much as possible nearby healthy tissues, the physician could prescribe thresholds for ablation coverage in all regions of interest, e.g. a given minimum (and/or maximum) volume fraction t of a k-th structure is ablated. For this purpose, the following quadratic ablation coverage-based objective functions might be used as optimization constraints:

$$f^{min}(A) = H(t - v_k(A, S_k))\left(\frac{t - v_k(A, S_k)}{t}\right)^2 \quad \text{(E4)}$$

$$f^{max}(A) = H(v_k(A, S_k) - t)\left(\frac{t - v_k(A, S_k)}{t}\right)^2 \quad \text{(E5)}$$

Here, $H(\cdot)$ is the Heaviside step function, t is the prescribed minimum (maximum) ablation fractional volume threshold, and $v_k$ indicates the current ablated fractional structure volume produced by the composite ablation A (see Equ. E3).

All mathematical objectives $f_i(A)$ are given as functions of the composite ablation zone binary mask A produced by all selected ablation applicator configurations (Equ. E2). The following composite objective function $$F(A) = \sum_{i=1}^{m} w_i f_i(A) + w_R R(A) \quad \text{(E6)}$$

can be defined and minimized to achieve the wished ablation coverage.

The quantities $w_i$ and $w_R$ represent manually set importance weights for all ablation coverage-based objective functions and a regularization term, respectively. The regularization term R(A) is optional, and might have different forms. This can be used to enforce some requested specific ablation zone characteristics. For example, we could use a Tikhonov regularization to avoid a too high cardinality (i.e. size) for the composite ablation binary mask A, or a regularization term to control (e.g. reduce) the size of the overlaps (i.e. intersections) among all delivered applicators' ablation binary masks leading to redundant ablations of tumor sub-regions.

As a next step, optimal discrete applicator configurations are selected as follows: It is assumed that a discrete set C of $N_c$ applicator configurations is given, and for each configuration c-th an ablation binary mask $A_c$ has been computed. P is defined as the set of currently selected applicators configurations, and A its corresponding composite (i.e. union) ablation zone binary mask computed as indicated in Equ. E2.

A goal for some examples that use set covering greedy iterative algorithm is to add to the selection set P a new applicator configuration c* which can potentially lead to an improved value of the ablation-based function F (A) at Equ. (E6). For the selection of the best applicator configuration, at current step n, an objective function value $f_c$, i.e. a coverage-based functional value, is computed for each possible c-th applicator configuration by:

$$f_c = F(A \cup A_c),\ c = 1, \ldots , N_c. \tag{E7}$$

Here, c represents the index of the ablation applicator configuration, and $N_c$ is the total number of applicators' configurations in the discrete set C. At each iteration n, the applicator configuration c* corresponding to the minimum objective function value is selected and added to the optimal set P of applicator configurations:

$$c^* = \min\{f_c\},\ c = 1, \ldots , N_c. \tag{E8}$$

In this example a greedy iterative algorithm is disclosed where a number of optimal applicator configurations are progressively selected. The selection of the best applicator configuration requires to compute the functional objective $f_c=F(A\cup A_c)$ for all $N_c$ ablation device configurations at each algorithm iterate. As a consequence, all ablated fractional structure volumes $v_k$ (Equ. E3) are recomputed at each algorithm n-th iteration for all $N_c$ ablation device configurations. These volumetric computations can represent a serious bottleneck for the algorithm performances. In order to speed-up these $v_k$ computations the following equation can be used:

$$v_k(A \cup A_c, S_k) = v_k(A, S_k) + v_k(A_c, S_k) - v_k(A \cap A_c, S_k). \tag{E9}$$

Here, on the right size of the Equ. E9, the $v_k(A_c, S_k)$ quantities can be precomputed at beginning, the $v_k$ (A, $S_k$) values are given and known from the previous algorithm iteration, while only the final term $v_k(A\cap A_c, S_k)$ may be computed to get the new $v_k(A\cup A_c, S_k)$ value for all $N_c$ ablation device configurations. Since the cardinality of the intersection set $(A\cap A_c)$ is obviously smaller than the cardinality of the union set $(A\cup A_c)$, computing $v_k$ $(A\cup A_c, S_k)$ using the Equ. 9 can drop enormously the required computation time.

Subsequently, an iterative local refinement of the selected applicator configurations is conducted. Given a new set P of selected applicator configurations from a previous step, the corresponding applicators' spatial positioning and delivered ablation binary mask can be locally refined by solving a mixed discrete-continuous iterative constrained optimization problem. This local refinement step is not mandatory, and could be dropped when the spatial discretization used for the generation of the initial set C of applicator configurations at the initial step is considered accurate enough by the physician.

However, if a very coarse spatial discretization is used to reduce the computational burden, an iterative local refinement step can be performed to improve the precision of the delivered applicator configurations and consequently to increase the ablation coverage of the tumor. At each refinement iteration, firstly, the optimal local rigid transformations of all currently selected applicators' ablation masks are determined by minimizing an ablation-based functional related to the treatment goals.

Starting from an initially selected discrete applicator position and ablation binary mask, an optimal roto-translation transformation (R, t) is computed and applied to the applicator position/direction in order to increase the ablation coverage of the tumor. This can be achieved by minimizing the function introduced at Equ. E6

$$F(R_p, t_p) = F(A[R_p, t_p]) = \sum_{i=1}^{m} w_i f_i(A[R_p, t_p]) + w_R R(A[R_p, t_p]) \tag{E10}$$

with respect to the parameters of rigid transformations $R_p$, $t_p$ used to transform the selected applicator tip positions and directions and associated binary masks at each grid position x:

$$A[R_p, t_p](x) = \bigcup_{p\in P} A_p(R_p x + t_p) \tag{E11}$$

Optionally, lower and upper bounds could be enforced to the optimization problem in order to limit the optimization search to the feasible solution set containing only roto-translation transformations of the applicators that are clinically deliverable. Finally, as a result, optimal rigid transformation parameters $$(R_p^*, t_p^*)$$

for all selected applicator configurations are obtained. As a second local refinement step, the rigidly transformed applicators' positions are kept fixed and the corresponding delivered ablation binary masks $A_p$ are optimally updated. Here, all possible binary masks provided in the device manufacturers' specification are evaluated at current roto-translated applicators positions. Finally, the new set of ablation masks $A_p$ is selected that produces the minimum ablation-coverage objective functional value, i.e. minimum coverage-based functional value.

To reduce the computational cost of this local refinement step, one could limit the objective function evaluations to only update the ablation binary mask of the very last selected applicator configuration, while the binary masks of all other selected applicators are kept fixed. This iterative local refinement step will toggle between the applicator's positioning optimization and the optimal binary masks selection till a user-prescribed ablation-based objective functional precision, and/or a maximum number of local refinement iterations, is achieved.

Subsequently, the iterative optimization strategy is described. The procedure parameters $$(P, R_p^*, t_p^*)$$

are optimized in an iterative strategy that toggles between an optimal selection of applicator configurations out of an initial discrete set, and a local refinement of the currently selected applicator configurations using continuous optimization methods. Firstly, the best applicator configuration is selected out of a big set of discrete applicator configurations, then, during the second step, all currently selected applicators are locally repositioned to improve the total ablation coverage of the tumor, and so on.

The algorithm iterations will be stopped if/when a given relative ablation coverage-based functional F precision is achieved, and/or a given maximum number of selected ablation applicator was reached. In these cases, the last achieved solution with Nset selected applicators is returned.

Finally, to improve the total computation time, one could select more than one new applicator configuration at each iteration. This will reduce the number of function computations needed to find the best solution to the expense of some degradations in terms of ablation coverage quality.

The set of selected applicators' configurations P and the corresponding composite ablation zone A can be properly initialized by exploiting the clinical expert's a-priori knowledge. If no such initialization is available a completely empty initial setting (i.e. P=∅, A=∅) is assumed: then this iterative strategy will populate the P set with most promising applicator configurations.

The optimized plan can be delivered by clinical experts. Here, implanted applicators are continuously tracked in real-time. In the case of detected applicator tip misplacements with respect to the planned positions, these tracked misplacements can be taken into account to adaptively re-optimize the remaining set of applicators and the corresponding composite ablation in order to re-establish the expected plan quality.

Figure 4:
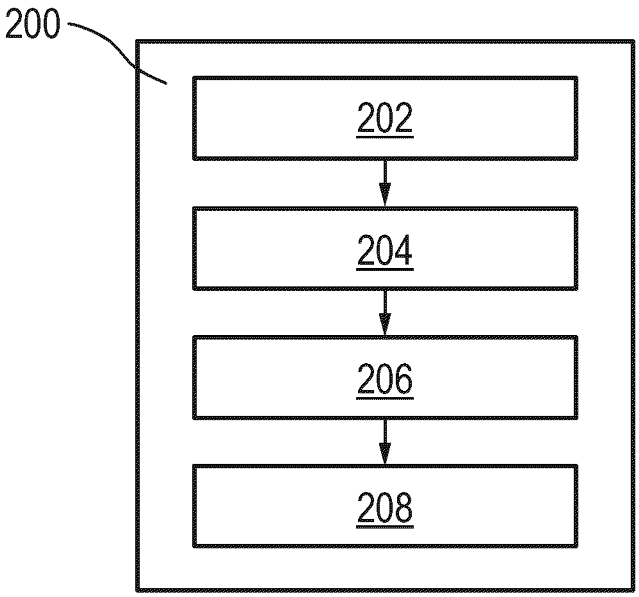
FIG. 4 illustrates a method for providing positioning support for treatment applicators.

FIG. 4 shows a related method 200 for providing positioning support for treatment applicators 8. The method 200 comprises providing 202 a distance r to be considered between entry points 10 and geometric information of a target to be treated, conducting 204 an optimization iteration step and determining which determines an optimal applicator configuration comprising selecting a first applicator entry point 10 based on the geometric information of the target to be treated, inactivating 206 all applicator entry points 22 within the distance r from the currently first selected applicator entry point 10 such that these entry points 22 are unavailable to further optimization iterations steps, conducting 208 a further optimization iteration step which determines and determining a further optimal applicator configuration comprising selecting a further applicator entry point 10 based on the geometric information of the target to be treated.

The iteration steps which determine an optimal applicator configuration comprising selecting a first applicator entry point 10 may again be based on the algorithm described above.

Figure 5:
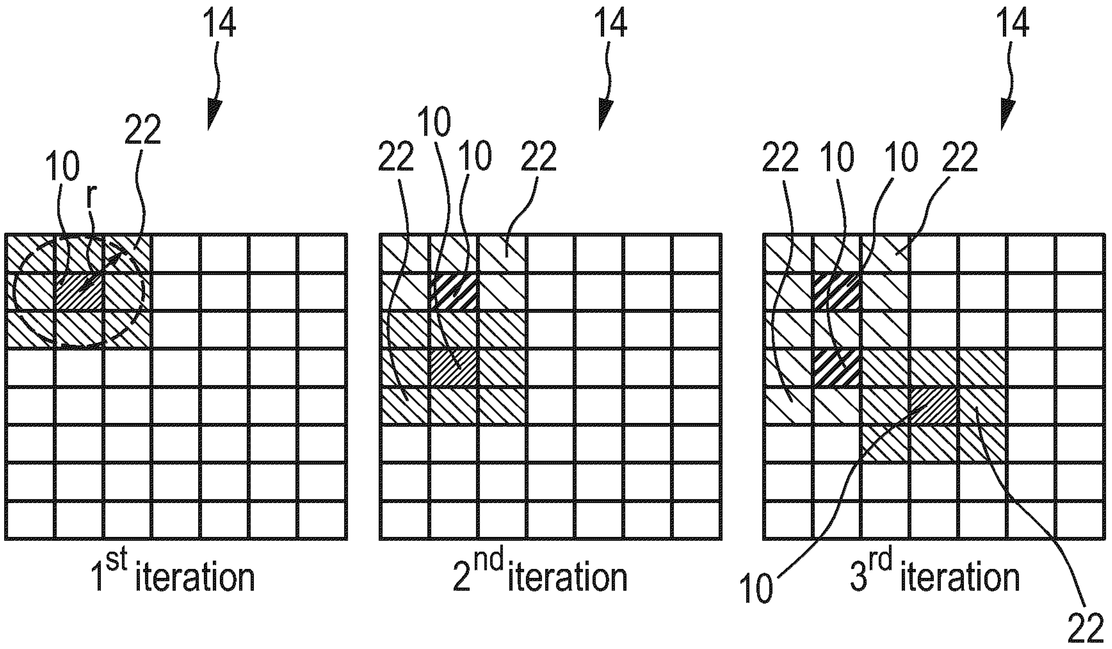
FIG. 5 illustrates the steps of the method, FIG. 6 provides an alternative example of an illustration of different steps of the method.
Figure 6:
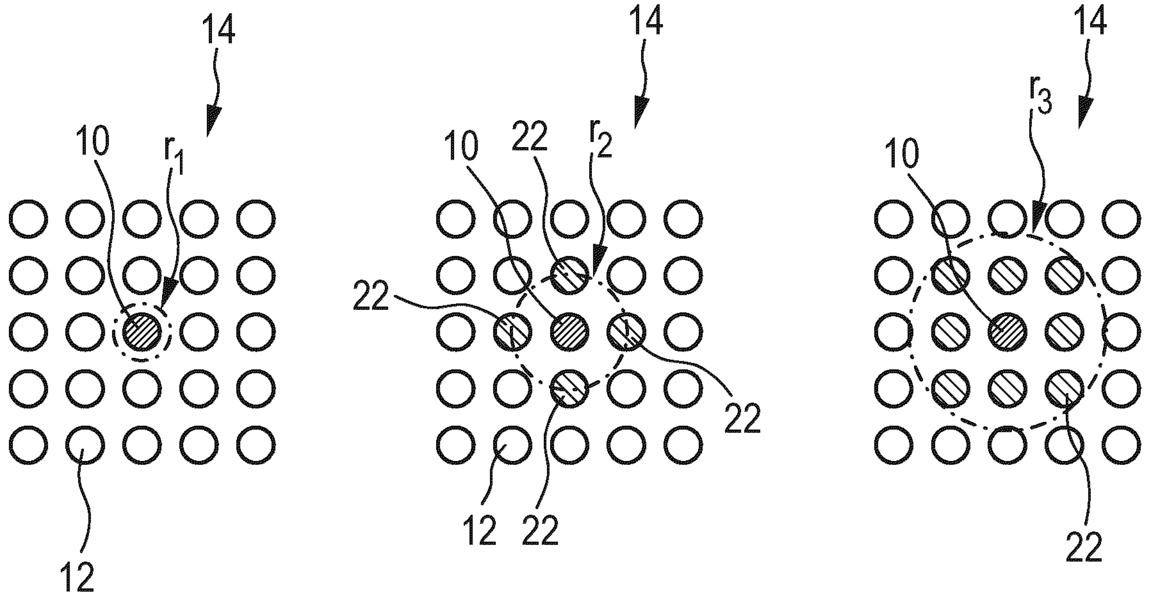

The steps conducted by the device 2 and the method 200 are illustrated with regard to FIG. 5 and FIG. 6. As shown in the left grid template 14 of FIG. 5, an optimization iteration has been conducted that includes an optimal applicator configuration comprising selecting an applicator entry point 10. As a next step, all entry points 22 within the distance r from the entry point 10 are inactivated such that these entry points 22 are unavailable to further optimization iterations. Afterwards, as shown in the grid template 14 arranged in the middle of FIG. 5, a further optimization iteration is conducted and a further optimal applicator configuration comprising selecting a further applicator entry point 10 is determined. Now again, all entry points 22 within a distance r from the now selected entry point 10 are inactivated. The iteration steps are conducted until no further optimal applicator configurations can be determined considering the inactivated entry points 22.

In other words, the inactivated entry points 22 form a circular inactivation mask, as shown in grey color enforced around each currently selected entry point 10. The method has the advantage to reduce the optimization freedom, also called solver freedom, only progressively along the iterations. At the very beginning, all entry points 10 or grid holes 12 will be active and selectable, however, the more the solver will select entry points 10 or grid holes 12 during iterations, the more constrained the solver search and solution space will become, since more and more entry points 10 will become inactive. The solution produced by the solver using such a technique will ensure a minimum distance r defined by the user is enforced.

FIG. 6 shows another example at which the proposed iterations are applied to a grid template 14, comprising grid holes 12 that are spaced apart from each other. For a small distance $r_1$, applicators 8 may be inserted into every grid hole 12. This is shown in the left of FIG. 6. When the distance is increased towards $r_2$ or $r_3$, such as shown in the middle template 14 or in the right template 14, grid holes 12 will be inactivated. As shown in the middle of FIG. 6, only grid holes 22 along a virtual vertical and horizontal axis (not shown in FIG. 6) through the entry point 10 will be deactivated. In the right grid template 14, also grid holes 22 that are diagonal to a virtual horizontal or vertical axis going through entry point 10 will be deactivated.

In general, the distance r may be a minimum distance in a template or a skin surface plane 16 (see FIG. 1), in particular a minimum Euclidean distance. The distance r may also be a maximum distance in the template or skin surface plane 16, in particular a maximum Euclidean distance. The distance r may also be a minimum and/or maximum distance between applicator trajectories 18 as shown in FIG. 3.

The optimization comprises a heuristic iterative discrete optimization. In the case of the applicator 8 being an ablation applicator 20, the optimization iteration considers at least one of the following: grid geometry information of a grid template 14, regional ablation coverage goals, manufacturer ablation zones for the selected applicator 8 to be used for the treatment, segmentation mesh considering regions of interest, in particular lesions and organs at risk, leading grid position. The grid geometry information of the grid template 40 may comprise at least one of the following: grid model, grid size, number of grid holes, distance between grid holes. The processor 6 of the device 2 as shown in FIG. 2 may further be configured to conducting a refinement iteration at which an optimal applicator configuration is removed from the solution and replaced by a new optimal applicator configuration. In one embodiment, the refinement iteration can comprise removing optimal applicator configurations one-by-one. i.e. orderly, with each iteration step. For example, a list of applicators can be used, wherein in each iteration step of the refinement iteration an applicator configuration corresponding to an applicator of the list of applicators is removed. In this case the applicator configurations can be removed subsequently. i.e. as defined by the sequence of applicators on the list. Alternatively, the applicator configuration can be selected and removed that when removed from the current solution, does degrade the functional as little as possible. This applicator configuration can be regarded as the least optimal application configuration. i.e. the remaining applicator configurations have higher impact on the respective goal of the optimization. The respective least optimal application configuration can be determined based on coverage functional values that can be computed for a given set of applicators and ablation zones, for instance, utilizing equation E7 as described above. Moreover, also functional derivatives could be analytically computed or discretely approximated based on the coverage-based functional values, if needed, to determine the least optimal applicator configuration.

Figure 7:
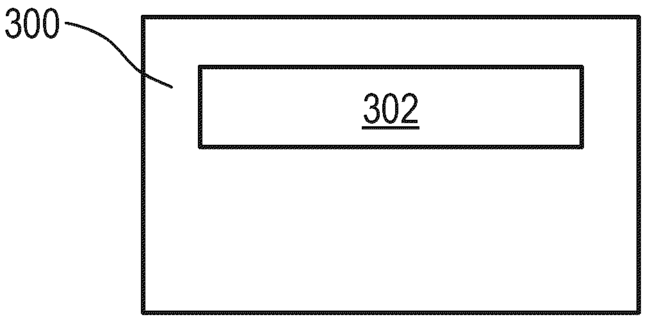
FIG. 7 illustrates a computer program for providing positioning support for treatment applicators.

FIG. 7 shows a computer program 300. The computer program 300 provides support for position planning for treatment applicators 8. The computer program 300 comprises program code means 302 for causing a computer to carry out the steps of the method as shown in FIG. 4.

The device 2 or the method 200 may further be configured to provide at least one of the following delivery parameters: Brachytherapy catheters positions, thermal ablation propositions, dual times, ablation times/power values. With the help of the method 200 or the device 2, it is avoided to deliver ablation zones over grid holes 12 that are at a distance lower than the distance r prescribed by the user. The also leads to a reduced treatment execution complexity thanks to a reduced physical interference between applicators 8 and a reduced overlap among ablation zones which means a lower risk to treat the same tissue multiple times.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like conducting an optimization iteration or inactivating all applicator entry points within the distance from the currently selected entry point, et cetera, performed by one or several units or devices can be performed by any other number of units or devices. These procedures can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems. Any reference signs in the claims should not be construed as limiting the scope.

The invention relates to a planning device for providing positioning support for treatment applicators. The device comprises a providing unit configured for providing a distance to be considered between applicator entry points and a processor. It has been found that when utilizing treatment applicators, in particular ablation treatment applicators, placing two or more applicators closely together increases the risk of ablating and damaging more tissue than required for the therapy success. By configuring the processor to inactivate all entry points within a distance r from a currently selected entry point such that these entry points are unavailable to further optimization iterations, and then conducting a further optimization iteration, an optimal applicator configuration can be provided that is effective with regard to the therapy success while the risk of ablating more tissue than required is reduced.

The invention claimed is:

1. A planning device for positioning treatment applicators, comprising a processor; and a memory storing a computer program wherein the processor is configured to execute the computer program stored in the memory, and wherein when the computer program is executed, the processor is caused to:

determine an applicator configuration comprising a first applicator entry point, inactivate all entry points within a distance (r) from the first applicator entry point such that these entry points are unavailable to a subsequent applicator configuration determination, wherein the distance (r) is a distance between applicator entry points determine a subsequent applicator configuration comprising a further applicator entry point.

2. The planning device as defined by claim 1, wherein the device provides positioning support for ablation treatment applicators, and wherein the processor is further caused to:

receive three-dimensional (3D) medical image data descriptive of a subject, receive a desired ablation volume, wherein the desired ablation volume is registered to the 3D medical image data, receive one or more protected volumes, wherein the one or more protected volumes are registered to the 3D medical image data, generate a discrete set of ablation applicator positions registered to the 3D medical image data, receive a discrete set of ablation patterns, initialize a composite ablation binary mask registered to the 3D medical image data, and determine an unablated volume by comparing the composite ablation binary mask to the desired ablation volume, wherein the unablated volume is registered to the 3D medical image data, determine an applicator configuration comprising an applicator entry point using a chosen objective function dependent upon the one or more protected volumes, the unablated volume, the discrete set of ablation patterns, the discrete set of ablation applicator positions, and inactivated applicator entry points, wherein the applicator configuration specifies one of the discrete set of ablation applicator positions and one of the discrete set of ablation patterns, update the composite ablation binary mask by calculating a union between the composite ablation binary mask and the one of the discrete set of ablation patterns located at the one of the discrete set of ablation applicator positions.

3. The planning device as defined in claim 2, wherein the chosen objective function comprises a quadratic ablation coverage-based objective function, a minimum/maximum ablation coverage function, and a uniform quadratic coverage function.

4. The planning device as defined by claim 1, wherein the entry points are at least one of the following:

grid holes of a grid template, and skin entry points.

5. The planning device as defined by claim 1, wherein the distance (r) is at least one of the following:

minimum distance in a template or skin surface plane, or maximum distance in a template or skin surface plane.

6. The planning device as defined by claim 1, wherein the distance (r) is a minimum and/or maximum distance between applicator trajectories.

7. The planning device as defined by claim 1, wherein the processor is configured to perform further optimization iteration steps until no further optimal applicator configuration is determinable considering the inactivated entry points.

8. The planning device as defined by claim 1, wherein the processor is further caused to:

conduct a refinement iteration step at which an applicator configuration is removed from the solution and replaced by another applicator configuration, conduct a further optimization iteration step to determine an optimal applicator configuration.

9. The planning device as defined by claim 8, wherein in each refinement iteration step the applicator configuration to be removed is selected orderly from the optimal applicator configurations.

10. The planning device as defined by claim 8, wherein the refinement iterations step is stopped when every applicator configuration was removed once during the iterations or when the removed applicator configuration is determined again as the result of the refinement iteration step.

11. The planning device as defined by claim 8, wherein in each refinement iteration step the applicator configuration to be removed is selected based on coverage-based functional values or derivatives to select a least optimal applicator configuration.

12. The planning device as defined by claim 1, further comprising a graphical user interface to visualize at least one of the following:

optimal set of applicator positioning configurations, inactivated entry points, or distance (r) to be considered between entry points.

13. Ablation system comprising an ablation treatment applicator and a planning device as defined in claim 1.

14. The planning device of claim 1, wherein the determine an applicator configuration comprising a first applicator entry point is an optimization iteration step.

15. The planning device of claim 1, wherein the processor is further caused to receive the distance (r).

16. Planning method for positioning treatment applicators, the method comprising:

receiving a distance (r) between entry points and geometric information of a target to be treated, conducting, by a processor, an optimization iteration step which determines an optimal applicator configuration comprising a first applicator entry point, inactivating, by the processor, all applicator entry points within the distance (r) from the first applicator entry point such that these entry points are unavailable to further optimization iteration steps, conducting, by the processor, a further optimization iteration step which determines a further optimal applicator configuration comprising a further applicator entry point.

17. A non-transitory computer readable medium storing instructions that, when executed by a processor, cause the processor to:

receive a distance (r) between entry points and geometric information of a target to be treated, conduct an optimization iteration step which determines an optimal applicator configuration comprising a first applicator entry point, inactivate all applicator entry points within the distance (r) from the first applicator entry point such that these entry points are unavailable to further optimization iteration steps, conduct a further optimization iteration step which determines a further optimal applicator configuration comprising a further applicator entry point.

* * * * *